United States Patent [19]

Allan

[11] 4,388,303

[45] Jun. 14, 1983

[54] METHOD TO REDUCE ANIMAL BROWSING DAMAGE TO PLANTS EMPLOYING SELENIUM COMPOUND

[75] Inventor: George G. Allan, Seattle, Wash.

[73] Assignee: Board of Regents, University of Washington, Seattle, Wash.

[21] Appl. No.: 251,156

[22] Filed: Apr. 6, 1981

[51] Int. Cl.$^3$ ..................... A01N 43/64; A01N 59/02
[52] U.S. Cl. ........................................ 424/162; 71/31; 424/249
[58] Field of Search ..................... 424/162, 249; 71/31

[56] References Cited

U.S. PATENT DOCUMENTS 3,226,291 12/1965 Rediske et al. .................... 424/207

OTHER PUBLICATIONS

Ismallov, Chemical Abstracts, vol. 84:84841v, (1976).
More et al., (I), Chemical Abstracts, vol. 85:31965c, (1976).
Cary et al., Chemical Abstracts, vol. 84:57785y, (1976).
Gupta et al., Chemical Abstracts, vol. 94:138459d, (1981).
More et al. (II), Chemical Abstracts, vol. 94:82918h, (1981).
Kudryavtsev, Chemical Abstracts, vol. 93:219562p, (1980).
Dzhabrailov et al., Chemical Abstracts, vol. 86:42353y, (1977).
Agaev et al., Chemical Abstracts, vol. 86:42354z, (1977).
Shakuri, Chemical Abstracts, vol. 86:42356b, (1977).
Fatalieva et al., Chemical Abstracts, vol. 90:5138u, (1979).
Lewis et al., J. of Agricultural & Food Chemistry, vol. 14, (1966), pp. 638-640.

*Primary Examiner*—Allen J. Robinson
*Attorney, Agent, or Firm*—Seed, Berry, Vernon & Baynham

[57] ABSTRACT

A method to reduce animal browsing damage to plants comprises the step of inducing a nonphytotoxic dosage of selenium into the foliage of the plants at a level sufficient to repel animals. The method is particularly suited for use in reforestation of pines, firs, and other conifers. The selenium is systemically absorbed into the plants after application to the surrounding soil in the root zone. Selenium compounds having a valency of no more than $4^+$ are applied to the soil around the plants to induce absorption in a preferred method.

14 Claims, No Drawings

METHOD TO REDUCE ANIMAL BROWSING DAMAGE TO PLANTS EMPLOYING SELENIUM COMPOUND

DESCRIPTION

1 Technical Field

This invention relates to a method to reduce animal browsing damage to a plant by inducing a nonphytotoxic level of selenium in the foliage of the plant. Animals avoid browsing on selenium-doped foliage.

2. Background Art

During stand development of conifers like Douglas fir, animals cause the greatest economic damage. Usually the animals browse and clip the stems and foliage of seedlings and saplings; while occasionally root cutting, budding, barking, trampling, and pulling of seedlings occur. Either the seedlings are killed or their growth is markedly suppressed by the browsing of big game (deer, bear, elk, and the like), hares and rabbits, grouse and other birds, beaver, gophers and other small rodents, domestic stock, and porcupines.

Four principal approaches are available for avoiding or controlling animal-caused damage to forest trees and their seedlings:

(1) reduce the animal population;
(2) exclude the animals from the plants mechanically;
(3) repel the animals from browsing; and
(4) alter silviculture practices.

Mechanical protection is the best in terms of damage prevented, but it is among the most expensive safeguards. Silviculture practices include (a) planting resistant species, (b) planting larger seedlings, (c) planting faster growing species, (d) removing and controlling other available food supplies in the plantation which might attract animals, and (e) cutting and replanting in arrangements which deter browsing.

Chemical repellents which affect either odor or taste are of two kinds—systemic and contact. A systemic repellent is applied to the foliage, roots, or soil (in the root zone), is absorbed into the plant, and is translocated to all parts of the plant. A contact repellent is applied to the foliage and stems of plants and remains on the surface of the plants to treat them. Two common contact repellents are tetramethylthiuram disulfide and zinc dimethyldithiocarbamate cyclohexamine. When used with conifers, these repellents are usually either sprayed onto the plants at the nursery or the plants are dipped prior to planting. Both are usually applied in 10% concentration in a water solution containing latex adhesives, thickening agents, and defoaming agents. Other contact repellants include a putrified fish fraction (PFG), fermented eggs (EV repellent), and human hair.

Systemic repellents offer many advantages over contact repellents, especially in that they provide greater resistance to weathering over longer periods of time. Induced systemic repellency has long been sought, but only with this invention has a safe and effective system been developed. The occurrence of selenium in certain plants is an example of a natural systemic animal repellent, and experiments have shown that animals prefer a selenium-free diet when good forage is available. Plants containing as little as 6–7 $\mu$g/g of selenium have been found to display natural repellency. The selenium-doped plants often act as insect repellents, perhaps by emitting volatile selenium compounds, such as dimethyl selenide or dimethyl diselenide.

Rediske and Lawrence investigated induced animal repellency by using selenate compounds ($SeO_4^=$) as systemic or contact repellents. 8 *Forest Science*, vol. 2, at 142–148 (1962). Sodium selenate applied as a surface coating (5000 ppm Se) was an effective repellent; in fact, it was more effective than the standard tetramethylthiuram disulfide contact repellent. As a systemic repellent, however, the experiments of Rediske and Lawrence showed that selenate was a failure. At the maximum allowable concentration in the Douglas firs tested, the selenate did not repel animals from browsing. Above 0.5 $\mu$g/g, the selenate was toxic to the Douglas fir seedlings.

In their article in 14 *J. Agri. Food Chem.*, no. 6, at 638 (1966), Lewis, Johnson, and Delwiche disclosed that plants treated with selenite ($SeO_3^=$) release volatile selenium compounds, such as dimethyl selenide, in quantities 10–15 times greater than selenate-treated plants.

DISCLOSURE OF INVENTION

This invention presents a simple, safe, and effective method of inducing systemic animal repellency in plants to reduce browsing damage otherwise caused by animals. The method is particularly useful with reforestation of evergreens, such as pine, Douglas fir, and other conifers. A level of selenium, such as selenite, is induced systemically into the foliage and stems of plants in a sufficient amount to repel animals from browsing without damaging the plants. That is, the level of selenium in the foliage is a nonphytotoxic amount capable of reducing or eliminating browsing damage caused by animals. Ordinarily, the unnaturally high level of selenium will be induced into the foliage by applying a selenium-containing compound, such as $Na_2SeO_3$, $(NH_4)_2SeO_3$, melamine selenite, and other selenites; $SeO_2$; FeSe; or mixtures thereof, to the soil so that the roots absorb the selenium and translocate it to the foliage. Applying an effective but nonphytotoxic dosage of selenium reduces browsing damage by repelling animals, such as deer, elk, bear, and other big game; hares and rabbits; grouse and other birds; beaver; gophers, mice, and other small rodents; domestic stock; and porcupines, without hindering seedling development.

BEST MODE FOR CARRYING OUT THE INVENTION

When induced into the foliage of plants, selenium, particularly in the form of selenite ($SeO_3^=$) applied to the soil, acts as a systemic repellent to reduce damage caused by animal browsing. This invention relates to a method to induce this artificially high level of selenium in the foliage. In particular, one method of inducing the level is to apply a selenium compound to the soil around a seedling so that the roots can absorb the selenium into its system and translocate the absorbed selenium to the foliage. Selenium in the foliage is a particularly desirable systemic repellent. Tetravalent selenium, such as selenite ($SeO_3^=$), can be applied to plants like Douglas fir in sufficient quantities to act as a repellent yet without killing the plant. Other forms of selenium having a valency of 4+ or less may be applied to the soil. Selenate compounds should be avoided because they have been found to have a low phytotoxicity level in plants such as Douglas fir.

Because of its potential to reduce browsing damage in reforestation, and because of the interest in systemic repellents in the forest products industry, this discussion will focus on tests conducted on conifers, particularly Douglas fir seedlings. The examples which follow are meant to illustrate the invention rather than to limit it. The method is applicable to all plants which exhibit a tolerance to selenium such that an absorbed amount present in the foliage will reduce browsing yet will not kill the plant. The method is particularly applicable to reforestation with evergreens, such as Douglas fir, pines, and other conifers. Because the economic loss due to browsing can be great, the method may still be applicable when the dosage level causes all but the hardiest of plants to die. One-third of the seedlings may be killed, in some circumstances, without the level being excessive. Therefore, the term "nonphytotoxic" should be interpreted liberally to include dosage levels which do kill some plants while allowing hardier plants to grow unimpaired.

This invention will probably be best understood with reference to the following examples.

EXAMPLE 1

To test whether selenium compounds can be systemically absorbed and translocated to the foliage, Douglas fir seedlings were treated with various levels of selenium in the tetravalent state. One, 10, 100, and 1000 mg doses of $SeO_2$ and $Na_2SeO_3$ were applied to the soil of potted Douglas fir seedlings. Foliage from the seedlings was collected at various times and was analyzed to determine the selenium content. Table 1 shows the results of the analysis four weeks after applying the selenium compounds. Selenium has moved through the roots of the Douglas fir seedlings into the foliage.

TABLE 1

| Compound | Application Level (mg) | Selenium Content in Foliage (μg/g) |
|---|---|---|
| $SeO_2$ | 1 | 1.75 |
| | 10 | 44.6 |
| | 100 | 398.1 |
| | 1000 | 646.2 |
| $Na_2SeO_3$ | 1 | 39.6 |
| | 10 | 41.1 |
| | 100 | 177.9 |
| | 1000 | 3446.3 |

EXAMPLE 2

In solution culture, various levels of $Na_2SeO_3$ were applied to Douglas fir seedlings. For dosages of 10, 20, 40 and 80 mg of $Na_2SeO_3$ in two liters of Hoaglund's solution, all seedlings showed a rate of selenium buildup in the foliage which declined as equilibrium was approached.

EXAMPLE 3

To determine the effect of the cation on the extent of selenium absorption, seedlings were treated individually with $Na_2SeO_3$ and $(NH_4)_2SeO_3$ (10 mg Se) in solution. Table 2 shows the selenium content in the foliage. Selenium is absorbed faster initially if applied in the form of $Na_2SeO_3$ rather than as $(NH_4)_2SeO_3$. The difference in the absorption rate may be due to the difference in the basicity of NaOH and $NH_4OH$, yet the difference in the absolute amounts absorbed tends to disappear as treatment continues.

TABLE 2

| Time (weeks) | Selenium content in foliage μg/g | |
|---|---|---|
| | $(NH_4)_2Se(O_3$* | $Na_2SeO_3$* |
| 1 | 0.94 | 6.5 |
| 2 | 8.6 | 13.9 |
| 3 | 12.4 | 14.3 |

*Application level 10 mg (selenium basis).

EXAMPLE 4

Analysis of the roots, stem, and branches as well as the foliage was made to determine how absorbed selenium is distributed in Douglas fir seedlings. The roots always had the highest level, usually well above that of the stem, branches, and foliage. All parts show an increase in selenium content upon treatment. The level in the stem, branches, and foliage is relatively equal; if significant, the foliage usually has the lowest amount of selenium.

EXAMPLE 5

To determine the phytotoxic level of tetravalent selenium upon Douglas fir, a series of tests on Douglas fir seedlings were conducted. Varying amounts of selenium were applied to seedlings, and their growth was observed. Table 3 summarizes these tests.

TABLE 3

| Compound | Selenium Application Level (mg) | Foliage Content (μg/g) | Observation |
|---|---|---|---|
| $SeO_2$ | 1 (pot) | 18 | no damage |
| | 10 " | 45 | no damage |
| | 100 " | 398 | ⅓ dead |
| | 1000 " | 646 | all dead |
| $Na_2SeO_3$ | 1 (pot) | 40 | no damage |
| | 10 " | 41 | no damage |
| | 100 " | 178 | ⅓ dead |
| | 1000 " | 3446 | all dead |
| $Na_2SeO_3$ | 10 (solution) | 104 | no damage |
| | 20 " | 314 | no damage |
| | 40 " | 575 | dried foliage |
| | 60 " | 692 | dried foliage |
| | 80 " | 832 | dried foliage |

Dried foliage indicates the first stages of death in the plant. The phytotoxic level is difficult to determine from these results. While one-third of the seedlings died at a foliage content of 178 μg/g when $Na_2SeO_3$ was applied to the soil, no damage occurred when the level reached 314 μg/g in solution culture. Only one-third were killed at a level of 398 μg/g when $SeO_2$ was applied to the soil. For reforestation purposes, a level of less than about 400 μg/g in the foliage probably will be useable without undue damage to the seedlings (even though some deaths are induced). Levels below about 200 μg/g are preferred.

The tests show that absorption of selenium is a function of the compound applied and the conditions in which the selenium is applied. In solution culture, the seedlings absorbed much more selenium for the same dosage level than when selenium was applied to the soil. Soils differ in composition; it is likely that seedlings in these different soils will display different absorption characteristics.

EXAMPLE 6

Tests were conducted to determine whether selenized seedlings provided any repellency to animal browsing. In the laboratory, selenized and non-selenized Douglas fir foliage was placed in the cages of rabbits. The selenized foliage contained between about 10-20 μg/g of selenium. The tests revealed that the consumption of selenized foliage was less than the nonselenized, verifying that the rabbits preferred the nonselenized foliage.

EXAMPLE 7

Field tests were conducted to determine whether selenized Douglas fir would be an effective means for reducing deer browsing. Seedlings were treated by applying solutions of $Na_2SeO_3$, each containing 40 mg of selenium. In two plantations (Discovery Bay and the Pack Forest), no browsing damage occurred throughout a four-week study. Deer were observed in the plantations, and browsing did occur on seedlings which were untreated.

EXAMPLE 8

Field tests showed that the level of selenium in the foliage fluctuated during the period following application, reaching a peak and then declining. Selenium is diffused from the foliage in volatile compounds, such as dimethyl selenide. Also, the level of selenium in the soil decreases because the selenium is leached away from the plant's root zone by rain and is converted to nonabsorbable forms of selenium by biological action. To make the dosage level more uniform over time, tests were conducted to determine whether ferroselenium (FeSe) would be an effective controlled release composition. Ferroselenium is an inexpensive, high selenium content powder which is water insoluble. The ferroselenium is nonabsorbable in its selenide form; through chemical conversion in the soil, however, the ferroselenium provides absorbable selenium compounds. Damage occurred in the seedlings, probably because the selenium was oxidized to both selenite ($SeO_3^=$) and selenate ($SeO_4^=$). As already discussed, selenate is toxic to Douglas fir at low dosage (about 0.5 μg/g). Therefore, care must be taken if FeSe is applied, although it does present some potential as a time-release composition.

EXAMPLE 9

Tests were conducted to determine whether selenium compounds can be systemically absorbed and translocated to the foliage of other conifers. Ponderosa pine, white pine, and Western red cedar were treated with various levels of $SeO_2$ by application to the soil around seedlings. Foliage was collected and analyzed to determine the selenium content. Tables 4 and 5 show the results of these tests. Selenium was absorbed into the seedlings and moved through the roots into the foliage.

TABLE 4

| Species | Application Level (mg) | Selenium Content in Foliage (μg/g) |
|---|---|---|
| Ponderosa pine | 0 | 0 |
|  | 10 | 0 |
|  | 20 | 2 |
|  | 100 | 5 |
|  | 500 | 50 |
| White pine | 0 | 0 |
|  | 10 | 4 |
|  | 20 | 4 |
|  | 100 | 50 |
|  | 500 | 485 |
| Western red cedar | 0 | 0 |
|  | 10 | 5 |

TABLE 4-continued

| Species | Application Level (mg) | Selenium Content in Foliage (μg/g) |
|---|---|---|
|  | 20 | 4 |
|  | 100 | 9 |
|  | 500 | 119 |

TABLE 5

The survival of conifer seedlings one week after application of various amounts of selenium dioxide

| Species | Level of Application, mg Se/Seedling | | | | |
|---|---|---|---|---|---|
|  | 0 | 10 | 20 | 100 | 500 |
| Ponderosa pine | 100% | 100% | 100% | 75% | 50% |
| White pine | 100 | 100 | 100 | 0 | 0 |
| Western red cedar | 100 | 75 | 100 | 0 | 0 |

Further tests are necessary to determine the phytoxocity level of selenium in these species, but the tests confirm the ability to absorb selenium systemically.

I claim:

1. A method to reduce reforestation damage to evergreen seedlings caused by animal browsing comprising the step of applying a compound selected from the group consisting of $Na_2SeO_3$, $(NH_4)_2SeO_3$, and $SeO_2$ to the soil around a seedling to promote systemic absorption so that foliage of the seedling contains a level of selenium which repels animals but which is substantially nonphytotoxic to the seedling.

2. The method of claim 1 wherein the selenium compound is $(NH_4)_2SeO_3$.

3. The method of claim 1 wherein the selenium compound is $SeO_2$.

4. The method of claim 1 wherein the selenium compound is $Na_2SeO_3$.

5. A method to reduce reforestation damage to conifer seedlings caused by animal browsing comprising the step of applying a compound selected from the group consisting of $Na_2SeO_3$, $(NH_4)_2SeO_3$, and $SeO_2$ to the soil around a conifer seedling to promote systemic absorption so that foliage of the seedling contains a level of selenium which repels animals but which is substantially nonphytotoxic to the seedling.

6. The method of claim 5 wherein the selenium compound is $(NH_4)_2SeO_3$.

7. The method of claim 5 wherein the selenium compound is $SeO_2$.

8. The method of claim 5 wherein the selenium compound is $Na_2SeO_3$.

9. A method to reduce reforestation damage to Douglas fir seedlings caused by animal browsing comprising the step of applying a compound selected from the group consisting of $Na_2SeO_3$, $(NH_4)_2SeO_3$, and $SeO_2$ to the soil around a Douglas fir seedling to promote systemic absorption of selenium into the seedling so that foliage of the seedling contains a level of selenium which repels animals but which is substantially nonphytotoxic to the seedling.

10. The method of claim 9 wherein the selenium compound is $(NH_4)_2SeO_3$.

11. The method of claim 9 wherein the selenium compound is $SeO_2$.

12. The method of claim 9 wherein the selenium compound is $Na_2SeO_3$.

13. A method to reduce reforestation damage to a Douglas fir caused by animal browsing comprising the step of applying to the soil around the Douglas fir a selenium compound selected from the group consisting of $Na_2SeO_3$, $(NH_4)_2SeO_3$, and $SeO_2$ to promote systemic absorption of the selenium into the Douglas fir so that the foliage contains a level of selenium which repels animals from browsing but which is substantially nonphytotoxic to the Douglas fir.

14. A method to reduce reforestation damage to Douglas fir caused by animal browsing comprising the step of applying a selenium compound selected from the group consisting of $Na_2SeO_3$, $(NH_4)_2SeO_3$, and $SeO_2$ to the soil around the Douglas fir to promote systemic absorption of the selenium into the Douglas fir so that the foliage contains between about 20–400 $\mu g/g$ of selenium.

* * * * *